United States Patent [19]  [11] 4,006,069
Hiratsuka et al. [45] Feb. 1, 1977

[54] SUPPORT FOR ELECTROPHORETIC ANALYSIS

[75] Inventors: Nobuo Hiratsuka; Nakatsugu Yaginuma, both of Minami-ashigara, Japan

[73] Assignee: Fuji Photo Film Co., Ltd., Minami-ashigara, Japan

[22] Filed: Nov. 17, 1975

[21] Appl. No.: 632,884

[30] Foreign Application Priority Data

Nov. 15, 1974 Japan .......................... 49-131828

[52] U.S. Cl. .......................... 204/180 G; 23/230 B; 204/299 R
[51] Int. Cl.² .................. G01N 27/26; G01N 27/28
[58] Field of Search ........... 204/180 G, 299, 230 B, 204/253 R

[56] References Cited

UNITED STATES PATENTS

| | | | |
|---|---|---|---|
| 3,255,100 | 6/1966 | Raymond | 204/180 G |
| 3,582,490 | 6/1971 | Zemel | 204/180 G |
| 3,622,484 | 11/1971 | Cawley | 204/180 G |
| 3,635,808 | 1/1972 | Elevitch | 204/180 G |
| 3,960,499 | 6/1976 | White | 204/180 G X |

*Primary Examiner*—Arthur C. Prescott
*Attorney, Agent, or Firm*—Sughrue, Rothwell, Mion, Zinn & Macpeak

[57] ABSTRACT

A support for use in electrophoretic analysis comprising a porous polymeric flat plate such as filter paper, cellulose acetate or a non-woven fabric and a polymeric gel, such as polyacrylamide gel, enclosed in the open cells of the flat plate. The gel membrane is tough and does not shrink upon drying. The support can also be used as a filter.

15 Claims, No Drawings

SUPPORT FOR ELECTROPHORETIC ANALYSIS

BACKGROUND OF THE INVENTION

1. FIELD OF THE INVENTION

This invention relates to a material comprising a porous polymeric plate having a polymeric gel enclosed therein, more specifically, to a material suitable for use as a support plate in electrophoretic analysis.

2. DESCRIPTION OF THE PRIOR ART

Electrophoretic methods can be classified as free electrophoretic methods in which an electrode is directly inserted into a sample solution without using a support and zone electrophoretic methods in which a solvent is included in a support and the solute is migrated therein. Zone electrophoretic methods have high utilitarian value because of the characteristic features thereof. For example, complete separation of the sample can be effected and dyeing or other chemical reactions can take place on the support. Moreover, either small or large samples can be handled. Zone electrophoretic methods are very effective for analyzing and isolating proteins such as blood serums.

Depending upon the support plate used, zone electrophoretic methods can be further classified into filter paper electrophoretic methods, cellulose acetate electrophoretic methods, agar electrophoretic methods, polyacrylamide gel electrophoretic methods and starch gel electrophoretic methods. In these methods the support plate includes filter paper or a sheet such as an acetate film, a polymeric gel membrane such as agar, polyacrylamide or starch, or a polymeric gel supported on a carrier such as a glass sheet or a plastic film.

The present invention is directed to an improvement in the support used in electrophoresis consisting of a polymeric gel supported on a carrier.

In order to perform electrophoresis using a polymeric gel supported on a carrier, it has previously been the practice to use a support prepared by sealing a polymeric gel in a tube (column) of glass or a plastic or a support prepared by placing a polymeric gel on a sheet of glass or plastic. The preparation of the columnar supports, however, requires substantial expertise, and it is time-consuming and troublesome to place the gel into columns one at a time. Furthermore, due to dispersion in support preparation, the precision of analyzing samples suffers. The high cost of such column materials is also a drawback.

On the other hand, it is also time-consuming and troublesome to prepare supports by placing a gel on a sheet, and manufacturing difficulties are often encountered, for example, the gel tends to break when coating the sample on the support.

Furthermore, when it is desired to dry and store electrophoretically recorded images after fractionating a sample on the support, the gel tends to come off the sheet because of shrinkage, or curling takes place, or the gel is very susceptible to breakage. Hence, meticulous care and expert skills are required for electrophoretic analysis using such a material.

SUMMARY OF THE INVENTION

Accordingly, it is one object of this invention, to overcome the defects of the conventional electrophoretic analysis methods and to provide a support for electrophoresis which has superior quality and operability.

Another object of this invention is to provide a tough support for electrophoresis which permits easy coating of a sample thereon and which is free from the danger of rupturing or injuring the polymeric gel at the time of coating a sample thereon.

Still another object of this invention is to provide a support for electrophoresis which does not shrink upon drying after electrophoresis and which can be stored without harm for extended periods of time.

Still a further object of this invention is to provide a support for electrophoresis which has a tough gel membrane, and permits operations such as dyeing, decolorization or densitometry to be easily performed after electrophoresis.

The above objects of this invention can be achieved by a support for electrophoresis comprising a porous polymeric flat plate having a polymeric gel enclosed in the open cells of the plate.

DETAILED DESCRIPTION OF THE INVENTION

The electrophoretic support of this invention can be prepared by the following method. A porous polymeric flat plate containing many pores, which pores consist of continuous open cells (the term "continuous open cells" used herein means those which pass through the plate, often called "pores"), such as a cellulose acetate porous membrane, filter paper, a polyamide resin, a polyvinyl chloride resin, a cellulose ester such as nitrocellulose, cellulose acetate butyrate, cellulose propionate, etc., or a non-woven fabric, is immersed in a polymeric sol or a monomer solution before polymerization to permit the sol or monomer solution to enter the pores. Where difficulty is encountered in getting the sol or solution into the pores this operation can be carried out in vacuum. After sufficient infiltration, the porous polymeric flat plate is withdrawn. Both surfaces of the plate are then placed between flat sheets, such as glass sheets, and a gel membrane is formed by gellation or polymerization. When the gellation or polymerization is completed, the flat sheets are removed, and there is thus obtained a support for electrophoresis comprising a porous polymeric flat plate having a polymeric gel in the formerly open cells of the plate.

The porous polymeric flat plate used in this invention has a porosity of about 10 to about 90%, preferably 50 to 90%. Porosity is calculated in accordance with the following equation:

$$\text{Porosity} = \frac{\text{Total volume of pores}}{\text{Total volume of plate (including pores)}} \times 100(\%)$$

Porous cellulose acetate films used as the porous polymeric flat plate in this invention can be selected from those described in Japanese Patent Publications 15698/68 and 40426/71. There is no particular restriction on the pore size of the porous cellulose acetate film, but it is preferably about 0.1 to about 10 microns.

Filter paper as can be used in this invention can be selected from those which are generally used in electrophoretic analysis methods and which are commercially available and have a porosity as specified above. Specifically, Watman No. 1 and No. 4 (W & R Balston) and Toyo Filter Paper No. 51 and No. 51A (Toyo Filter Paper Mfg. Co., Ltd.) are preferred.

Non-woven fabrics as can be used in this invention can be selected from those which have a porosity as specified above and a thickness of about 0.05 to about 1.0 mm. Non-woven fabrics of polyesters, polyethylene, polystyrene or nylon are preferred.

Certain most preferred flat plates do exist, and these can be described as follows: cellulose acetate of a thickness of 0.05 to 1 mm, a porosity of 10 to 90% and a cell size of 0.1 to 50 $\mu$, preferably 0.1 to 10 $\mu$; filter paper of a thickness of 0.05 to 1 mm, a porosity of 10 to 60%, and a cell size of 1 to 100 $\mu$, preferably 5 to 20 $\mu$ (mean cell size); and non-woven fabric of a thickness of 0.05 to 1 mm, a porosity of 10 to 90% and a cell size of 0.1 to 100 $\mu$, preferably 1 to 20 $\mu$.

The polymeric gel of this invention preferably is neutral, i.e., it does not itself possess a charge and is gel-forming and transparent. Useful gels are swellable with water, and those having more than a 100% water content, where "water content" is represented by:

$$\frac{\text{Gel weight at saturation swelling} - \text{Dry gel weight}}{\text{Dry gel weight}} \times 100(\%)$$

For instance, in Example 1, the polyacrylamide had a water content about 500% and in Example 2 the agar had a water content of about 400%. Specific examples include agar such as a commercially available agar, e.g., Special Novel Agar and Bacto Agar, both produced by Difco Laboratory, Ion Agar produced by Oxoid Company, Agar-agar produced by Merck & Co., starch such as Starch Hydride for Electrophoresis produced by Sigma Chemical Company, acrilic amide such as Cyanogum 41 produced by American Cyanamide Company, and the like.

Gels which can be used in conventional electrophoresis where the polymeric gel is coated on a polyester support can be employed in the present invention, so long as they meet the above criteria.

In the preparation of the support in accordance with this invention, both surfaces of the porous polymeric plate are held by flat, non-porous sheets, e.g., glass, during gel formation. This is because if the gel is formed not only in the pores of the plate but also on the surface of the plate, the strength of the polymeric gel membrane is lowered, and, at the same time, it is likely to lead to errors in electrophoretic analysis.

A gel membrane of polyacrylamide can be prepared by dissolving acrylamide in a buffer solution at a pH of about 8 to 9, such as a tris-citric acid buffer and, depending on the end use, adding a cross-linking agent such as N,N'-propylenebis-acrylamide or N,N'-methylenebis-acrylamide in an amount of about 0.5 to 30 wt%, preferably 1 to 5 wt%, based on the amount of acrylamide employed, a polymerization initiator such as ammonium persulfate, a light sensitizer such as riboflavin or eosine, and a polymerization promoter such as tetramethylenediamine, infiltrating the resultant polyacrylamide solution into the porous polymeric plate in the manner described hereinabove, and then forming the gel membrane of polyacrylamide by photopolymerization or radical polymerization, e.g., by exposure of about more than 1,000 lux, preferably about 3,000 to about 20,000 lux, in general, with white light such as from a fluorescent lamp, preferably light having wavelength of about 300 to 400 nm.

A gel membrane of starch or agar can be prepared by first preparing a starch, agar or acrylic amide sol by methods well known in the art, and then infiltrating the sol into the porous polymeric plate in the manner described above and cooling the plate to form the gel membrane. The exact cooling procedure chosen in accordance with the present invention is not overly important, and typically the gel is merely permitted to cool to room temperature at a natural rate.

For the embodiment where a sol is formed, the size of the sol can be freely selected without limitation.

For both the monomer polymerization and the sol embodiment, however, certain preferred concentrations exist for the systems. For example, for an agar sol it is preferred to use from about 0.5 to about 5.0% by weight agar, most preferably 1 to 2 weight % agar, for a starch sol it is preferred to use from about 5 to about 20 weight % starch, most preferably 13 to 15 weight % starch, and when acrylic amide monomer is polymerized, it is preferred to use from about 1 to about 50 weight % acrylic amide, most preferably 3 to 30 weight % acrylic amide, all based on the total system weight.

Aqueous polymerization systems or sols are preferred, and the infiltration is conveniently performed at a pressure of 0 atmosphere and to 1 atmosphere at a temperature of from about 15° to about 100° C. There is no specific limitation as to the time of the infiltration, but usually infiltration is completed in less than about 2 to 3 minutes.

Since the electrophoretic support of this invention retains the gel in the pores of the porous plate, the gel membrane is tough as compared with conventional gel supports which have a gel membrane on the surface thereof, and easy coating of samples to be analyzed is possible. In addition, the electrophoretic support of this invention permits coating of samples at constant quantities using a micropipette, which has been impossible with the conventional gel membrane supports. Thus, analysis and separation of the samples can be performed quantitatively.

Since the gel membrane in the support of this invention is tough, it does not break during use, and various operations such as electrophoresis, dyeing, decolorization and densitometry can be easily carried out.

Furthermore, since the gel membrane in the support of this invention does not substantially shrink upon drying after electrophoresis, it does not curl, come off the support or break. Thus, it can be handled easily without the meticulous care required for prior art supports.

The support of this invention can be produced in large quantities at one time, and this insures uniform properties, whereby reproducibility of the electrophoretic analysis and sample isolation capability increase strikingly.

The electrophoretic support of this invention can also be used as a filter, for example, in the ultra filtration of water-soluble high molecular weight compounds such as proteins, nucleic acid, etc. Thus, according to this invention, a soft material such as gel which has been difficult to use as a filter material because of its poor strength can now be used as a filter.

In the following Examples illustrate the present invention in greater detail. It should be noted that these Examples do not limit the scope of this invention.

EXAMPLE 1

Electrophoretic support consisting of a cellulose acetate membrane filter into which a polyacrylamide gel has been infiltrated:

A container was filled with a solution of 14.3 g of acrylamide, 750 mg of N,N'-methylenebis-acrylamide and 0.4 mg of riboflavin in 300 cc of a 0.08M tris-citric acid buffer solution (pH: 8.30). A 140 micron thick cellulose acetate membrane filter (MICROFILTER-FM-300, trademark for a product of Fuji Photo Film Co., Ltd.; porosity: 75%; cell size: 3 μ) was immersed in the solution at atmospheric pressure and at room temperature (about 23° C) for 30 seconds. After infiltration of the solution into the filter, it was withdrawn from the vat. The filter was then placed between two glass sheets which enclosed the surfaces of the same, and exposed to a fluorescent lamp for 1 hour (output of lamp: 20 w; distance from lamp: 10 cm) to form a gel membrane. All operations before exposure were carried out in the dark. It is to be noted that at the thickness involved in this example there is no difference if exposure is from both sides of the gel membrane to be formed or only from one side.

The resulting electrophoretic support was permitted to dry in the air and mounted on an electrophoretic microanalyzer (a product of Joko Sangyo Kabushiki Kaisha), and electrophoresis of a blood serum was performed at a constant current of 0.2 mA/cm for 2 hours in a discontinuous buffer system using a 0.3 mole boric acid-sodium hydroxide buffer (pH: 8.4) as an electrode solution, that is, an anodic solution and a cathodic solution were placed in different vessels and each contacted with the electrophoretic support via a filter paper (the electrode solutions were subjected to capillary rise from the vessels to the electrophoretic support via the filter paper in a conventional manner).

The gel membrane exhibited its inherent properties, and the electrophoresis resulted in the fractionation of a blood serum into 10 fractions.

The electrophoresis was repeated, and the accuracy of repeated reproduction was compared with using a conventional polyester support having a polyacrylamide gel membrane on the surface thereof. It was found with the conventional gel membrane support that the dispersion of accuracy in repeated reproductions was 10%, whereas it was 2% with the support in accordance with this invention, a substantial improvement in the accuracy of reproducible results.

Furthermore, the conventional polyacrylamide gel membrane shrank considerably upon drying after electrophoresis, and curled. Sometimes, in fact, the gel membrane separated from the polyester film. On the other hand, the gel membrane in the support of this invention did not substantially shrink, and substantially no curling occurred.

Throughout the entire procedure, the support in accordance with this invention lent itself to far easier handling than the conventional support.

EXAMPLE 2

Electrophoretic support consisting of a filter paper and an agar gel infiltrated thereinto:

One gram of Bacto Agar (a product of Difco Laboratory) was dissolved in 100 cc of 0.07M Veronal (buffer (pH: 8.60)) by heating to boil, and the solution placed in a container. A filter paper (Toyo Filter Paper No. 51, 200 microns thick; porosity: 40%) was immersed in the solution. After sufficient infiltration at atmospheric pressure at 50° C for 1 minute, the filter paper was taken out and placed between two glass sheets. It was maintained for 1 hour at 20° C to form a gel membrane.

The support obtained was permitted to dry in the air and mounted on the same electrophoretic microanalyzer as was used in Example 1, and electrophoresis of a blood serum was carried out at a constant current of 0.5 mA/cm for 2 hours using 0.07M Veronal (buffer) as an electrode solution.

The electrophoresis resulted in the separation of the blood serum into five fractions, and the support showed the same fractionating ability as a conventional agar gel support.

The accuracy of repeated reproduction was examined in the same manner as in Example 1. It was found that with the conventional support, the accuracy of reproduction (dispersion) was 8%, whereas it was 2% with the support of this invention) showing an improvement in result reproducibility.

The shrinkage of the gel membrane upon drying was strikingly reduced in the support of this invention as compared with the conventional agar gel support.

Furthermore, the support of this invention contained a tough gel membrane, and was far easier to handle than the conventional agar gel support.

While the invention has been described in detail and with reference to specific embodiments thereof, it will be apparent to one skilled in the art that various changes and modifications can be made therein without departing from the spirit and scope thereof.

What is claimed is:

1. In an electrophoretic analysis process utilizing a supported analysis member, the improvement wherein said supported analysis member comprises a porous polymeric flat plate and a polymeric gel enclosed in the open cells of the flat plate.

2. A method for producing a support for electrophoretic analysis which comprises enclosing a sol in the pores of a porous polymeric flat plate and thereafter gelling the same.

3. A method for producing a support for electrophoretic analysis which comprises enclosing a monomer in the pores of a porous polymeric flat plate and thereafter polymerizing the same to form a gel.

4. A support for electrophoretic analysis comprising a porous polymeric flat plate and a polymeric gel enclosed in the open cells of the flat plate.

5. The support of claim 4, wherein the flat plate has a porosity of about 10 to about 90%.

6. The support of claim 1, wherein the pore size of the flat plate ranges from 0.1 to 100 μ.

7. The support of claim 4, wherein the flat plate is a cellulose acetate membrane or non-woven fabric membrane.

8. The support of claim 5, wherein the flat plate is a cellulose acetate of a non-woven fabric having a porosity of 50 to 90%.

9. The support of claim 5, wherein the flat plate is a filter paper having a porosity of 10 to 60%.

10. The support of claim 7, wherein the cellulose acetate membrane has a pore size of 0.1 to 10 microns.

11. The support of claim 4, wherein the polymeric gel is a polyacrylamide gel.

12. The support of claim 4, wherein the polymeric gel is an agar gel.

13. The support of claim 4, wherein the polymeric gel is a starch gel.

14. A filter consisting of a porous polymeric flat plate and a polymeric gel sealed in the open cells of the flat plate.

15. The filter of claim 14, wherein the porous polymeric flat plate is a cellulose acetate membrane.

* * * * *